(12) United States Patent
Higashi et al.

(10) Patent No.: US 10,497,486 B2
(45) Date of Patent: Dec. 3, 2019

(54) ROBUST SENSING FILM FOR FIRE GASES

(71) Applicant: Honeywell International Inc., Morris Plains, NJ (US)

(72) Inventors: Robert E. Higashi, Shorewood, MN (US); Karen M. Newstrom-Peitso, Hopkins, MN (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 273 days.

(21) Appl. No.: 15/377,471

(22) Filed: Dec. 13, 2016

(65) Prior Publication Data
US 2018/0164239 A1   Jun. 14, 2018

(51) Int. Cl.
| | |
|---|---|
| *H01B 1/02* | (2006.01) |
| *H01B 1/08* | (2006.01) |
| *C04B 35/495* | (2006.01) |
| *C01G 41/02* | (2006.01) |
| *G01N 27/12* | (2006.01) |
| *G01N 33/00* | (2006.01) |

(52) U.S. Cl.
CPC ............... *H01B 1/02* (2013.01); *C01G 41/02* (2013.01); *C04B 35/495* (2013.01); *G01N 27/125* (2013.01); *G01N 27/127* (2013.01); *G01N 33/0036* (2013.01); *G01N 33/0037* (2013.01); *H01B 1/08* (2013.01); *C04B 2235/3258* (2013.01); *G01N 27/128* (2013.01); *Y02A 50/245* (2018.01)

(58) Field of Classification Search
CPC . H01B 1/02; H01B 1/08; C01G 41/02; G01N 27/125; G01N 27/127; G01N 33/0036; G01N 33/0037; G01N 33/0044; G01N 27/128; C04B 35/495; C04B 2235/3258; Y02A 50/242; Y02A 50/245
See application file for complete search history.

(56) References Cited

U.S. PATENT DOCUMENTS

| | | | | |
|---|---|---|---|---|
| 4,313,338 A * | 2/1982 | Abe | ....................... | G01N 27/12 338/34 |
| 8,573,030 B2 * | 11/2013 | Gole | .................... | G01N 27/127 324/649 |
| 8,578,758 B2 * | 11/2013 | Ito | ........................ | G01N 27/127 204/424 |
| 2012/0161790 A1 * | 6/2012 | Smith | .................. | G01N 27/125 324/658 |

OTHER PUBLICATIONS

Authors: M G Hutchins et al, Title: Electrical conduction mechanisms in thermally evaporated tungsten trioxide (WO3) thin films, Date: Oct. 20, 2006, Publisher: Journal of Physics: Condensed Matter, vol. 18 , pp. 9987-9997.*

Some. Webster's II New Riverside University Dictionary. (Year: 1988).*
LeGore et al. "Aggregation and sticking probability of gold on tungsten trioxide films," Sensors and Actuators B, 76, pp. 373-379. (Year: 2001).*
Anisimov et al. "The Microstructure and Properties of Thin WO3 Films Modified by Gold," Russian Journal of Physical Chemistry A, vol. 84, No. 7, pp. 1220-1125. (Year: 2010).*
Othman et al. "Response Enhancement of WO3 Gas Sensors by Metallic Nanograins," 2013 IEEE Sensors. (Year: 2013).*
Smith, D. J., et al., "Stability, Sensitivity and Selectivity of Tungsten Trioxide Films for Gas Sensing Applications", *5th Technical Digest, IEEE Solid-State Sensor and Actuator Workshop*, (1992), 78-81.
Tao et al: "H2S sensing properties of noble metal doped WO3 thin film sensor fabricated by micromachining", Sensors and Actuators B: Chemical: International Journal Devoted to Research and Development of Physical and Chemical Transducers, Elsevier BV, NL, vol. 81, No. 2-3, Jan. 5, 2002 (Jan. 5, 2002), pp. 237-247.
Penza et al: "NOx gas sensing characteristics of WO3 thin films activated by noble metals (Pd, Pt, Au) layers", Sensors and Actuators B: Chemical: International Journal Devoted to Research and Development of Physical and Chemical Transducers, Elsevier BV, NL, vol. 50, No. 1, Jul. 15, 1998 (Jul. 15, 1998), pp. 52-59,.
Othman et al: "Response Enhancement of WO3 Gas Sensors by Metallic Nanograins", 2013 IEEE Sensors, Nov. 3, 2013 (Nov. 3, 2013), pp. 1-4.
Legore et al: "Aggregation and sticking probability of gold on tungsten trioxide films", Sensors and Actuators B: Chemical: International Journal Devoted to Research and Development of Physical and Chemical Transou, Elsevier BV, NL, vol. 76, No. 1-3, Jun. 1, 2001 (Jun. 1, 2001), pp. 373-379.
International Search Report and Written Opinion for corresponding International Application No. PCT/US2017/064930 dated Feb. 20, 2018, 10 pages.
Anisimov et al: "The microstructure and properties of thin WO3 films modified by gold", Russian Journal of Physical Chemistry A, vol. 84, No. 7, Jan. 1, 2010 (Jan. 1, 2010), pp. 1220-1225.

* cited by examiner

*Primary Examiner* — Matthew R Diaz
(74) *Attorney, Agent, or Firm* — Alston & Bird LLP

(57) ABSTRACT

A gas sensor that includes a heat source and a gas sensing film. The gas sensing film includes a polycrystalline tungsten trioxide film thermally connected to the heat source and a plurality of islands of gold on a surface of the polycrystalline tungsten trioxide film. The surface of the polycrystalline tungsten trioxide film is exposed between the islands of gold to allow the polycrystalline tungsten trioxide film to sense gas. A first electrode that electrically connected to the polycrystalline tungsten trioxide film and a second electrode is electrically connected to the polycrystalline tungsten trioxide film. The resistance of the polycrystalline tungsten trioxide film between the first electrode and the second electrode changes when the polycrystalline tungsten trioxide film is exposed to a particular type of gas.

18 Claims, 5 Drawing Sheets

ROBUST SENSING FILM FOR FIRE GASES

BACKGROUND

Metal Oxide Semiconductor (MOS) gas sensors that utilize tungsten trioxide (WO3) films are typically very sensitive to surface interactions with gases. This sensitivity of the WO3 films to surface interactions with gases is important in determining the presence of gases.

SUMMARY

A gas sensing film that includes a polycrystalline tungsten trioxide film and a plurality of islands of gold on a surface of the polycrystalline tungsten trioxide film. The surface of the polycrystalline tungsten trioxide film is exposed between the islands of gold to allow the polycrystalline tungsten trioxide film to sense a gas.

A gas sensor comprising that includes a heat source and a gas sensing film. The gas sensing film includes a polycrystalline tungsten trioxide film thermally connected to the heat source and a plurality of islands of gold on a surface of the polycrystalline tungsten trioxide film. The surface of the polycrystalline tungsten trioxide film is exposed between the islands of gold to allow the polycrystalline tungsten trioxide film to sense gas. A first electrode that electrically connected to the polycrystalline tungsten trioxide film and a second electrode is electrically connected to the polycrystalline tungsten trioxide film. The resistance of the polycrystalline tungsten trioxide film between the first electrode and the second electrode changes when the polycrystalline tungsten trioxide film is exposed to a particular type of gas.

A method of fabricating a gas sensor that includes overlaying a tungsten trioxide film onto a first electrode and a second electrode and overlaying gold onto a surface of the tungsten trioxide film. The method further includes sintering the tungsten trioxide film and the gold to form a polycrystalline tungsten trioxide film that includes a plurality of islands of gold on the surface of the polycrystalline tungsten trioxide film.

DETAILED DESCRIPTION OF THE DRAWINGS

The embodiments of the present disclosure will be described, by way of example only, by reference to the FIGS. 1-6 of the accompanying drawing in which.

DETAILED DESCRIPTION

The following Detailed Description is merely exemplary in nature and is not intended to limit the subject matter or the application and uses of the same. Furthermore, there is no intention to be bound by any theory presented in the preceding background or the following detailed description.

WO3 films have historically been doped with gold to get selective hydrogen sulfide gas sensitivity at lower operating temperatures (e.g., 200 to 250 degrees centigrade). The WO3 films described herein are not doped with gold throughout the film but rather include islands of gold on the surface of the WO3 films. Including islands of gold on the surface of the WO3 films has been demonstrated to retain good nitrogen dioxide gas detection sensitivity even after the WO3 films have been exposed to various MEMS fabrication techniques.

Figure 1:
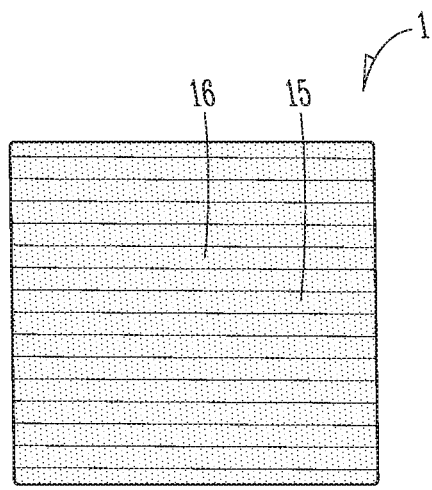
FIG. 1 shows a plan view of an example sensing film.
Figure 2:
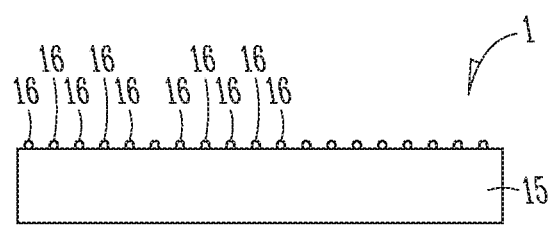
FIG. 2 shows a side view of the example sensing film shown in FIG. 1.

FIG. 1 shows a plan view of an example gas sensing film 1. FIG. 2 shows a side view of the example gas sensing film 1 shown in FIG. 1.

The gas sensing film 1 includes a polycrystalline tungsten trioxide film 15 and a plurality of islands of gold 16 on a surface of the polycrystalline tungsten trioxide film 15. The surface of the polycrystalline tungsten trioxide film is exposed between the islands 16 of gold to allow the polycrystalline tungsten trioxide film to sense a gas. The gas sensing films 1 described herein may have crystal grain sizes that are smaller than the electrode 14A, 14B (see, e.g., FIG. 4) spacing that is utilized in a subsequent gas sensor, resulting in more uniform film resistance and more reliable responses when particular gases are present.

In some forms, the polycrystalline tungsten trioxide film 15 has a thickness between 2000 and 5000 angstroms, and preferably has a thickness of about 4000 angstroms. It should be noted that when the polycrystalline tungsten trioxide film 15 has a thickness within this range, the gas sensing film 1, the gas sensing film 1 may have improved sensitivity and enhanced manufacturability.

Gas sensing films 1 are contemplated where at least some of the plurality of islands 16 of gold have a thickness in the range of about 1000 to 10,000 Angstroms. In addition, at least some of the plurality of islands 16 of gold may have a perimeter in the range of about 1 to 10 microns. When the plurality of islands 16 of gold approximate this size, the gas sensing film 1 inhibits the grains of tungsten trioxide film 15 from growing so large that there may be no grain boundaries between the electrodes 14A. 14B. This absence of grain boundaries may significantly reduce the sensitivity of the tungsten trioxide film 15.

FIGS. 3-6 shows all or part of a gas (e.g., nitrogen dioxide) sensor 10 (hereinafter also referred to as "sensor 10"), in accordance with at least one example. The gas sensor 10 can include a substrate 12 that may (or may not) be part of a MEMS structure. The substrate 12 may include at least one of silicon dioxide, silicon, quartz, glass, or the like. In an example, the substrate 12 can be formed of a flexible material such that the substrate 12 can conform to non-planar surfaces. In another example, the substrate 12 is not flexible. In some forms, the gas sensor 10 may be formed by a batch method.

The gas sensor 10 further includes a heat source 11 (see FIG. 3) and a gas sensing film 1 (similar to the gas sensing film 1 described above) that includes a polycrystalline tungsten trioxide film 15 thermally connected to the heat source 11. As discussed above, the gas sensing film 1 includes a plurality of islands 16 of gold on a surface of the polycrystalline tungsten trioxide film 15. The surface of the polycrystalline tungsten trioxide film is exposed between the islands 16 of gold to allow the polycrystalline tungsten trioxide film 15 to sense gas.

Figure 4:
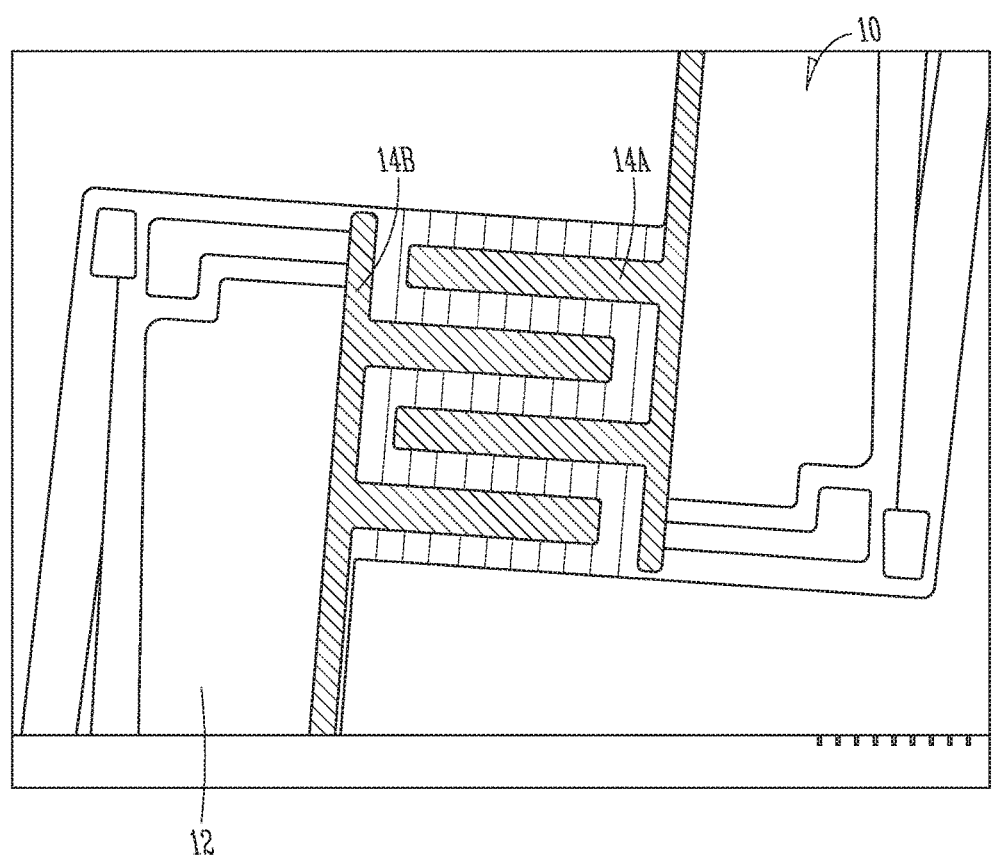
FIG. 4 is a plan view similar to FIG. 3 illustrating the example sensor with electrodes added to the sensor.
Figure 5:
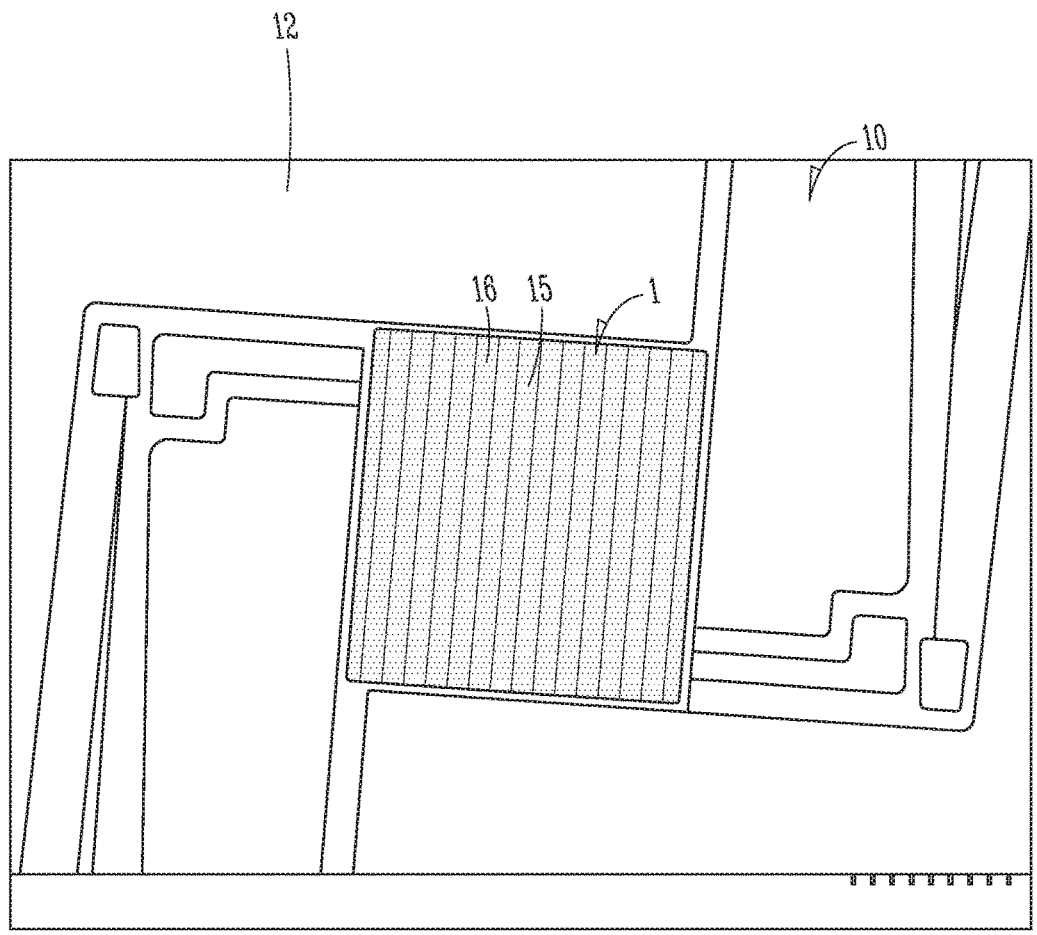
FIG. 5 is a plan view similar to FIGS. 3 and 4 illustrating the example sensor with a sensing film added to the sensor.
Figure 6:
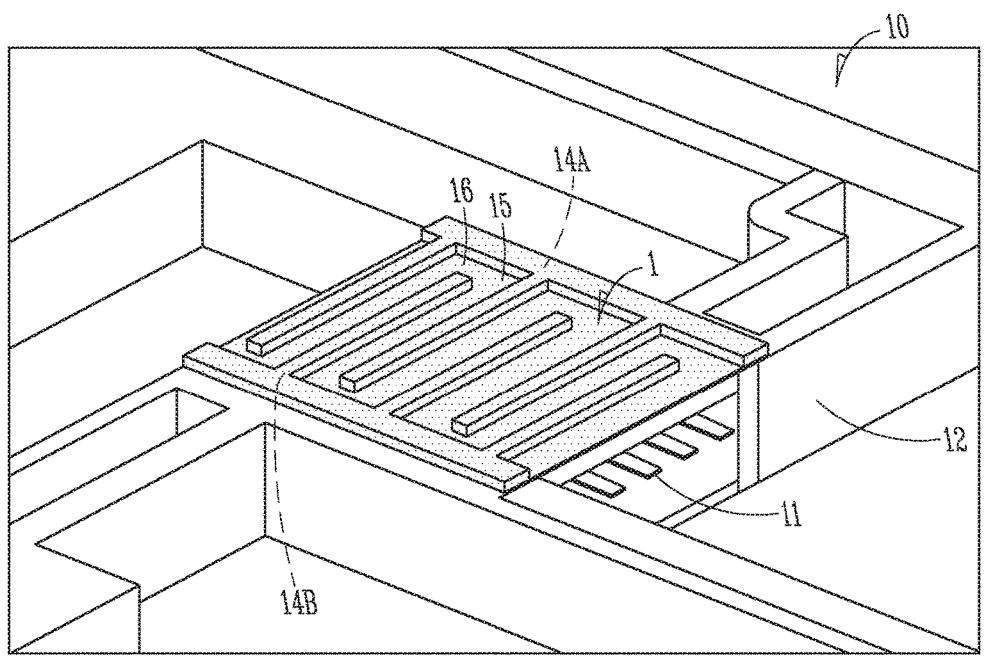
FIG. 6 shows a perspective view of the example sensor shown in FIG. 5.

A first electrode 14A (see FIG. 4) is electrically connected to the polycrystalline tungsten trioxide film 15 (see FIGS. 5 and 6). The gas sensor 10 further includes a second electrode 14B (see FIG. 4) that is electrically connected to the polycrystalline tungsten trioxide film 15 (see FIGS. 5 and 6). The resistance of the polycrystalline tungsten trioxide film 15 between the first electrode 14A and the second electrode 14B changes when the polycrystalline tungsten trioxide film 15 is exposed to a particular type of gas (e.g., nitrogen dioxide).

In some forms, the polycrystalline tungsten trioxide film 15 is electrically isolated from the heat source 11. In addition, the heat source 11 may be part of a mems structure or some type of wafer that is part of, or not part of a mems structure. The type of heat source 11 that is used in the gas sensor 10 will depend in part on manufacturing considerations and the amount of heat that is required when utilizing the gas sensor 10 (among other factors).

Figure 3:
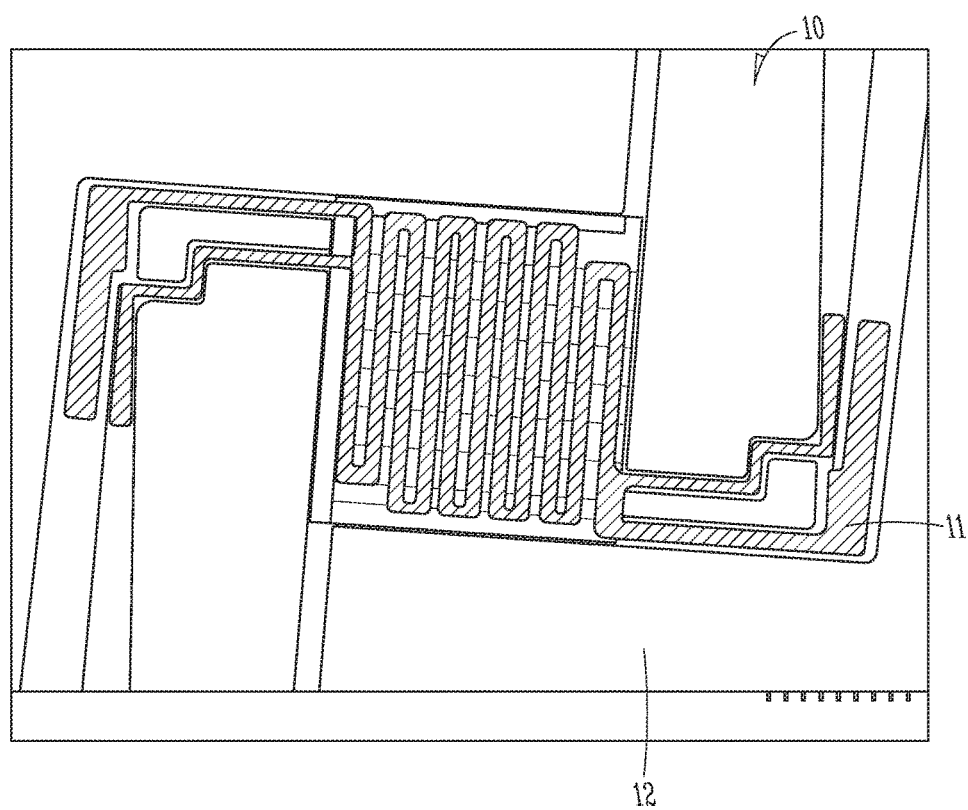
FIG. 3 is a plan view illustrating a portion of an example sensor where a heat source is shown.

In the example gas sensor 10 illustrated in FIGS. 3 and 6, the heat source 11 includes a platinum heating element. It should be noted that the platinum heating element may be part of, or not a part of, a mems structure.

As discussed above, the resistance of the polycrystalline tungsten trioxide film 15 between the first electrode 14A and the second electrode 14B may change when the polycrystalline tungsten trioxide film 15 is exposed to nitrogen dioxide. In some forms, the resistance of the polycrystalline tungsten trioxide film 15 between the first electrode 14A and the second electrode 14B may change when the polycrystalline tungsten trioxide film 15 is elevated to a temperature between 200 and 400° C. Elevating the temperature of the polycrystalline tungsten trioxide film 15 within this range may promote sensitivity to gas detection and enhance operating life.

As shown in the example of FIG. 4, the sensor 10 may include interdigitated electrodes (IDEs) 14A, 14B supported by the substrate 12. The IDEs may be supported by the substrate such as by depositing the IDEs on a surface of the substrate. Interdigitated electrodes 14A, 14B include two individually addressable interdigitated comb-like electrode structures. The IDEs 14A. 14B can include platinum/titanium, gold/chromium, gold/nickel silver, or the like.

As shown in FIGS. 5 and 6, the sensing film 1 may be configured to interact with a gas (e.g., nitrogen dioxide). That is, the sensing layer 16 may be in electrical contact with the IDEs 14A, 14B, such that conductivity of the sensor 10 may vary based on the interaction between the sensing film 1 and the IDEs 14A, 14B when in the presence of varying concentrations of a gas.

In the absence of a particular gas, the electrical resistance of the interaction between the sensing layer 16 and the IDEs 14A, 14B is relatively high. As an example, in the presence of nitrogen dioxide, the polycrystalline tungsten trioxide film 15 reacts with the nitrogen dioxide to increase the energy barrier such that the electrical resistance of the sensing layer 16 measured between the IDEs 14A. 14B increases. This change in electrical resistivity can be used to indicate the presence of nitrogen dioxide.

In some forms, the amount of change in electrical resistivity may indicate a concentration of nitrogen dioxide that is present near the sensor 10. The reaction between the p-type metal oxide and the nitrogen dioxide is reversible and, in the absence of nitrogen dioxide, the resistance decreases once again back towards levels approaching or equal to the original resistance.

Referring again to FIG. 4, the interdigitated electrodes 14A and 14B may be deposited on the substrate 12, (e.g., such as by a direct printing or photolithography methods). In an example, the sensing layer 16 can be deposited on the IDEs 14A, 14B so as to encompass the IDEs 14A, 14B and form a thin layer above the IDEs 14A. 14B. In an example, a thickness of the layer above the IDEs is about 0.2 µm, 0.4 µm, 0.6 µm, 0.8 µm, 1 µm, 1.2 µm, 1.4 µm, 1.6 µm, 1.8 µm, or 2.0 µm.

In an example, the gas sensor 10 may be configured to detect nitrogen dioxide at temperatures from about 200° C. to about 400° C. Therefore, the sensor 10 described herein may serve to sense nitrogen dioxide at elevated temperatures.

A method of fabricating a gas sensor 10 will now be described with reference to FIGS. 1-6. The method includes overlaying a tungsten trioxide film 15 onto a first electrode 14A and a second electrode 14B and overlaying gold 16 onto a surface of the tungsten trioxide film 15. The method further includes sintering the tungsten trioxide film 15 and the gold 16 to form a polycrystalline tungsten trioxide film 15 that includes a plurality of islands 16 of gold on the surface of the polycrystalline tungsten trioxide film 15.

In some forms, overlaying a tungsten trioxide film 15 onto a first electrode 14A and a second electrode 14B includes ion beam sputtering the tungsten trioxide film 15 onto the first electrode 14B and the second electrode 14B. As an example, ion beam sputtering the tungsten trioxide film 15 onto the first electrode 14A and the second electrode 14B may include ion beam sputtering with at least one of xenon, argon, or krypton gas present while the ion beam sputtering occurs. The manner in which the tungsten trioxide film 15 is applied onto the first electrode 14A and the second electrode 14B will depend in part on the type of gas sensor 10 that is being fabricated as well as other manufacturing and sensing considerations.

It should be noted that forms of the method are contemplated where overlaying gold 16 onto a surface of the tungsten trioxide film 15 includes evaporating the gold 16 onto the surface of the tungsten trioxide film 15. As an example, evaporating the gold 16 onto the surface of the tungsten trioxide film 15 may include applying the gold 16 with an electron beam evaporator. The manner in which the gold 16 is applied onto the surface of the tungsten trioxide film 15 will depend in part on the type of gas sensor 10 that is being fabricated as well as other manufacturing and sensing considerations.

In some forms, sintering the tungsten trioxide film 15 and the gold 16 to form a polycrystalline tungsten trioxide film 15 that includes a plurality of island 16 of gold on a surface of the polycrystalline tungsten trioxide film 15 may include heating the tungsten trioxide film 15 and the gold 16 in air in a temperature range between 450 to 600° C. Elevating the tungsten trioxide film 15 with the gold to this temperature range allows the gold to inhibit grain growth with the tungsten trioxide film 15 resulting in a relative larger number of grain boundaries between the electrodes 14A, 14B.

As an example the tungsten trioxide film 15 and the gold 16 may be heated to between 450 to 600° C. for between 2 and 8 hours. It should be noted that heating the tungsten trioxide film 15 and the gold 16 in this manner for this length of time may promote efficient fabrication of the gas sensing film 1.

During the sintering process, the tungsten trioxide film 15 may transform from an amorphous structure to a polycrystalline structure that is suitable for gas sensing. In some examples forms, tungsten trioxide may be applied to the IDE surface and areas between the IDEs 14A, 14B.

In other example forms, the gas sensing film 1 may be patterned in conjunction with a photoresist liftoff process that requires the photoresist to be patterned on the wafer (or MEMS structure) prior to the gas sensing film deposition. Once the gas sensing film 1 is applied, the photoresist field may then be dissolved thereby lifting off the unwanted film outside the gas sensing film 1 area.

Sintering the tungsten trioxide film 15 makes the tungsten trioxide film 15 film more gas sensitive by manipulating the gold into a plurality of islands 16 on the surface of the tungsten trioxide film 15. This process provides robust gas sensitivity for the tungsten trioxide film 15.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in this document, the terms "first," "second," and "third," etc. are used merely as labels, and are not intended to impose numerical requirements on their objects.

From the foregoing, it will be observed that numerous variations and modifications can be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Although a few embodiments have been described in detail above, other modifications are possible. For example, the logic flows depicted in the FIGS. do not require the particular order shown, or sequential order, to achieve desirable results. Other steps can be provided, or steps can be eliminated, from the described flows, and other components can be added to, or removed from, the described systems. Other embodiments can be within the scope of the following claims.

EXAMPLES

Examples of the present disclosure provide gas sensors including tungsten trioxide film.

Example 1 includes subject matter directed toward a gas sensing film comprising: a polycrystalline tungsten trioxide film; and a plurality of islands of gold on a surface of the polycrystalline tungsten trioxide film, wherein the surface of the polycrystalline tungsten trioxide film is exposed between the islands of gold to allow the polycrystalline tungsten trioxide film to sense a gas.

In Example 2, the subject matter of Example 1 can be optionally configured wherein the polycrystalline tungsten trioxide film has a thickness between 2000 and 5000 Angstroms.

In Example 3, the subject matter of Examples 1 or 2 can be optionally configured wherein the polycrystalline tungsten trioxide film has a thickness of about 4000 Angstroms.

In Example 4, the subject matter of Examples 1-3 can be optionally configured wherein at least some of the plurality of islands of gold have a thickness in the range of about 1.000 to 10,000 Angstroms.

In Example 5, the subject matter of Examples 1-4 can be optionally configured wherein at least some of the plurality of islands of gold have a perimeter of in the range of about 1 to 10 microns.

Example 6 includes subject matter directed toward s gas sensor comprising: a heat source; a gas sensing film that includes a polycrystalline tungsten trioxide film thermally connected to the heat source, wherein the gas sensing film includes a plurality of islands of gold on a surface of the polycrystalline tungsten trioxide film, wherein the surface of the polycrystalline tungsten trioxide film is exposed between the islands of gold to allow the polycrystalline tungsten trioxide film to sense gas; a first electrode that is electrically connected to the polycrystalline tungsten trioxide film; and a second electrode that is electrically connected to the polycrystalline tungsten trioxide film, wherein the resistance of the polycrystalline tungsten trioxide film between the first electrode and the second electrode changes when the polycrystalline tungsten trioxide film is exposed to a particular type of gas In Example 7, the subject matter of Example 6 can be optionally configured wherein the polycrystalline tungsten trioxide film is electrically isolated from the heat source.

In Example 8, the subject matter of Examples 6 or 7 can be optionally configured wherein the heat source is part of a MEMS structure.

In Example 9, the subject matter of Examples 6-8 can be optionally configured wherein the resistance of the polycrystalline tungsten trioxide film between the first electrode and the second electrode changes when the polycrystalline tungsten trioxide film is exposed to nitrogen dioxide.

In Example 10, the subject matter of Examples 6-9 can be optionally configured such that wherein the resistance of the polycrystalline tungsten trioxide film between the first electrode and the second electrode changes when the polycrystalline tungsten trioxide film is elevated to a temperature between 200 and 400 degrees centigrade.

In Example 11, the subject matter of Examples 6-10 can be optionally configured wherein the first electrode and the second electrode have an interdigitated configuration.

In Example 12, the subject matter of Examples 6-11 can be optionally configured wherein the heat source includes a platinum heating element.

In Example 13, the subject matter of Example 12 can be optionally configured wherein the platinum heating element is part of a MEMS structure.

Example 14 includes subject matter directed to a method of fabricating a gas sensor comprising: overlaying a tungsten trioxide film onto a first electrode and a second electrode; overlaying gold onto a surface of the tungsten trioxide film; and sintering the tungsten trioxide film and the gold to form a polycrystalline tungsten trioxide film that includes a plurality of islands of gold on the surface of the polycrystalline tungsten trioxide film.

In Example 15, the subject matter of Example 14 can be optionally configured wherein overlaying a tungsten trioxide film onto a first electrode and a second electrode includes ion beam sputtering the tungsten trioxide film onto the first electrode and the second electrode.

In Example 16, the subject matter of Examples 14 or 15 wherein ion beam sputtering the tungsten trioxide film onto the first electrode and the second electrode includes ion beam sputtering in the presence of at least one of xenon, argon or krypton gas.

In Example 17, the subject matter of Examples 14-16 wherein overlaying gold onto a surface of the tungsten trioxide film include evaporating the gold onto the surface the tungsten trioxide film.

In Example 18, the subject matter of Examples 14-17 wherein evaporating the gold onto the surface of the tungsten trioxide film includes applying the gold with an electron beam evaporator.

In Example 19, the subject matter of Examples 14-18 wherein sintering the tungsten trioxide film and the gold to form a polycrystalline tungsten trioxide film that includes a plurality of islands of gold on a surface of the polycrystalline tungsten trioxide film includes heating the tungsten trioxide film and the gold to between 475 to 600 degrees centigrade.

In Example 20, the subject matter of Example 19 wherein heating the tungsten trioxide film and the gold to between 475 to 600 degrees centigrade includes heating the tungsten trioxide film and the gold to between 475 to 600 degrees centigrade for between 2 and 8 hours.

What is claimed is:

1. A gas sensing film comprising:
   a polycrystalline tungsten trioxide film; and
   a plurality of islands of gold on a surface of the polycrystalline tungsten trioxide film, wherein the surface of the polycrystalline tungsten trioxide film is exposed between the islands of gold to allow the polycrystalline tungsten trioxide film to sense a gas, wherein two or more islands of gold of the plurality of islands of gold have a perimeter in the range of about 1 to 10 microns.

2. The gas sensing film of claim 1, wherein the polycrystalline tungsten trioxide film has a thickness between 2000 and 5000 Angstroms.

3. The gas sensing film of claim 1, wherein the polycrystalline tungsten trioxide film has a thickness of about 4000 Angstroms.

4. The gas sensing film of claim 1, wherein two or more islands of gold of the plurality of islands of gold have a thickness in the range of about 1,000 to 10,000 Angstroms.

5. A gas sensor comprising:
   a heat source;
   the gas sensing film according to claim 1 thermally connected to the heat source, wherein two or more islands of gold of the plurality of islands of gold have a thickness in the range of about 1,000 and 10,000 Angstroms;
   a first electrode that is electrically connected to the polycrystalline tungsten trioxide film; and
   a second electrode that is electrically connected to the polycrystalline tungsten trioxide film, wherein a resistance of the polycrystalline tungsten trioxide film between the first electrode and the second electrode changes when the polycrystalline tungsten trioxide film is exposed to nitrogen dioxide.

6. The gas sensor of claim 5, wherein the polycrystalline tungsten trioxide film is electrically isolated from the heat source.

7. The gas sensor of claim 5, wherein the heat source is part of a MEMS structure.

8. The gas sensor of claim 5, wherein the resistance of the polycrystalline tungsten trioxide film between the first electrode and the second electrode changes when the polycrystalline tungsten trioxide film is elevated to a temperature between 200 and 400 degrees centigrade.

9. The gas sensor of claim 5, wherein the first electrode and the second electrode have an interdigitated configuration.

10. The gas sensor of claim 5, wherein the heat source includes a platinum heating element.

11. The gas sensor of claim 10, wherein the platinum heating element is part of a MEMS structure.

12. A method of fabricating a gas sensor comprising:
    overlaying a tungsten trioxide film onto a first electrode and a second electrode;
    overlaying gold onto a surface of the tungsten trioxide film; and
    sintering the tungsten trioxide film and the gold to form a polycrystalline tungsten trioxide film that includes a plurality of islands of gold on the surface of the polycrystalline tungsten trioxide film, wherein the surface of the polycrystalline tungsten trioxide film is exposed between the islands of gold to allow the polycrystalline tungsten trioxide film to sense a gas, wherein two or more islands of gold of the plurality of islands of gold have a perimeter in the range of about 1 to 10 microns.

13. The method of claim 12, wherein overlaying a tungsten trioxide film onto a first electrode and a second electrode includes ion beam sputtering the tungsten trioxide film onto the first electrode and the second electrode.

14. The method of claim 12, wherein ion beam sputtering the tungsten trioxide film onto the first electrode and the second electrode includes ion beam sputtering in the presence of at least one of xenon, argon or krypton gas.

15. The method of claim 12, wherein overlaying gold onto a surface of the tungsten trioxide film includes evaporating the gold onto the surface of the tungsten trioxide film.

16. The method of claim 15, wherein evaporating the gold onto the surface of the tungsten trioxide film includes applying the gold with an electron beam evaporator.

17. The method of claim 12, wherein sintering the tungsten trioxide film and the gold to form a polycrystalline tungsten trioxide film that includes a plurality of islands of gold on a surface of the polycrystalline tungsten trioxide film includes heating the tungsten trioxide film and the gold to between 475 to 600 degrees centigrade.

18. The method of claim 17, wherein heating the tungsten trioxide film and the gold to between 475 to 600 degrees centigrade includes heating the tungsten trioxide film and the gold to between 475 to 600 degrees centigrade for between 2 and 8 hours.

* * * * *